United States Patent
Kronberg

Patent Number: 5,259,382
Date of Patent: Nov. 9, 1993

[54] OPTICAL TRANSCUTANEOUS BILIRUBIN DETECTOR

[76] Inventor: James W. Kronberg, 108 Independent Blvd., Aiken, S.C. 29801

[21] Appl. No.: 663,518

[22] Filed: Mar. 4, 1991

[51] Int. Cl.$^5$ .............................................. A61B 5/00
[52] U.S. Cl. ..................................... 128/633; 128/665
[58] Field of Search ...................... 128/633, 664, 665; 606/3

[56] References Cited

U.S. PATENT DOCUMENTS

| | | | |
|---|---|---|---|
| Re. 31,815 | 1/1985 | Alfano | 128/665 |
| 4,029,085 | 5/1977 | DeWitt et al. | 128/623 |
| 4,178,917 | 12/1979 | Shapiro | 128/665 |
| 4,236,526 | 12/1980 | Richard | 128/633 |
| 4,267,844 | 5/1981 | Yamanishi | 128/633 |
| 4,423,736 | 1/1984 | DeWitt et al. | 128/633 |
| 4,479,499 | 10/1984 | Alfano | 128/665 |
| 4,586,513 | 5/1986 | Hamaguvl | 128/633 |
| 4,836,206 | 6/1989 | Maxwell et al. | 128/633 |
| 4,877,034 | 10/1989 | Atkins et al. | 128/665 |
| 4,894,547 | 1/1990 | Leffell et al. | 128/633 |
| 5,069,214 | 12/1991 | Samaras et al. | 128/633 |
| 5,127,406 | 7/1992 | Yamaguchi | 128/633 |

FOREIGN PATENT DOCUMENTS

| | | | |
|---|---|---|---|
| 3137326 | 3/1983 | Fed. Rep. of Germany | 128/665 |
| 3931036 | 11/1990 | Fed. Rep. of Germany | 128/665 |
| 2658410 | 8/1991 | France | 128/665 |
| 8401665 | 12/1985 | Netherlands | 128/665 |

*Primary Examiner*—Lee S. Cohen
*Assistant Examiner*—Krista Pfaffle
*Attorney, Agent, or Firm*—Brian R. Tumm; Harold M. Dixon; William R. Moser

[57] ABSTRACT

A transcutaneous bilirubin detector comprising a source of light having spectral components absorbable and not absorbable by bilirubin, a handle assembly, electronic circuitry and a fiber optic bundle connecting the assembly to the light source and circuitry. Inside the assembly is a prism that receives the light from one end of the fiber optic bundle and directs it onto the skin and directs the reflected light back into the bundle. The other end of the bundle is trifucated, with one end going to the light source and the other two ends going to circuitry that determines how much light of each kind has been reflected. A relatively greater amount absorbed by the skin from the portion of the spectrum absorbable by bilirubin may indicate the presence of the illness. Preferably, two measurements are made, one on the kneecap and one on the forehead, and compared to determine the presence of bilirubin. To reduce the impact of light absorption by hemoglobin in the blood carried by the skin, pressure is applied with a plunger and spring in the handle assembly, the pressure limited by points of a button slidably carried in the assembly that are perceived by touch when the pressure applied is sufficient.

4 Claims, 2 Drawing Sheets

OPTICAL TRANSCUTANEOUS BILIRUBIN DETECTOR

The United States Government has rights in this invention pursuant to Contract No. DE-AC09-89SR18035 between the U.S. Department of Energy and Westinghouse Savannah River Company.

BACKGROUND OF THE INVENTION

1. Field of the Invention:

The present invention relates to an instrument for detecting the level of bilirubin in the skin. More particularly, the present invention relates to a noninvasive method of detecting bilirubin concentration in the skin of infants.

2. Discussion of the Background:

Bilirubin is a reddish to yellow pigment having the chemical formula $C_{33}H_{36}N_4O_6$ and consisting of a broken porphyrin ring which is produced in the metabolic breakdown of hemoglobin and other porphyrin-containing proteins. In an adult it is removed from the blood by the liver and forms the major pigment of bile, through which it is excreted from the body. However, the liver of a newborn child, and especially of a premature infant, is not yet mature and cannot process bilirubin in this way.

The birth process often results in extensive bruising of the newborn: blood escapes into the tissue and must then be broken down metabolically. Bilirubin forms and, since the liver cannot remove it, accumulates in the bloodstream. If levels rise high enough, it begins to be deposited in other body tissues. Its first and most visible appearance is in the skin, where it creates a form of jaundice. At still higher levels, deposition begins in deeper tissues, including the brain, and can result in permanent brain damage from kernicterus.

To prevent damage, an infant's bilirubin levels must often be closely monitored for the first several days, and sometimes several weeks, of life. Once detected, an excess is easily removed from the body by exposure to ordinary blue light, which is strongly absorbed by bilirubin converting it to an activated form more easily processed by the immature liver. Skin-deposited bilirubin and blood-borne bilirubin when circulating through vessels near the skin, can be purged from the body through simple skin exposure to sunlight, or to lamps with a high bluelight output ("bili lights") for several hours a day over the course of a week or so.

Skin deposition of bilirubin is not uniform over the body, but begins, and remains heaviest, in the face and upper body. The result is a yellowish tinge which appears first in the face and then, as deposition continues, both darkens and extends downward to other skin areas. Initial upper-body bilirubin deposition may have evolved as a survival mechanism, since these areas would have been the most often (and most directly) exposed to sunlight. Color comparison may be a reasonable, noninvasive method of monitoring bilirubin.

Color comparison is complicated by the fact that other pigments, besides bilirubin, are present in the skin. Chief among these are melanin, the normal brown pigment of skin, and hemoglobin in the surface blood vessels. Melanin is less of a problem than it might first appear to be. Melanin formation is a slow and complex process, typically incomplete until several months or even years of age: newborns, of whatever race, have relatively little. The amount of melanin present, moreover, is normally uniformly distributed in the skin (with the exception of the so-called "mongolian spot" in some racial groups) and thus will not cause an interfering color difference between properly-chosen upper and lower body sites. For practical purposes, therefore, this source of interference may be disregarded. Hemoglobin presents a potentially more severe problem, since its pattern of distribution (in blood vessels) is inherently uneven.

Bilirubin monitoring, however, usually requires blood analysis, and this poses a problem. Because an infant's circulatory system is not yet fully developed, blood must be drawn using a procedure called a "heel stick" in which one or more punctures are made in the heel and blood is repeatedly squeezed out into a collecting tube. Obtaining the several milliliters needed for the analysis can take as much as twenty minutes. The procedure is traumatic even for an infant in good health, and for a very premature infant adds stress which combined with other factors could actually be life-threatening. Because of this, bilirubin testing is usually only begun when, in the judgment of a health professional, an infant already shows visible signs of jaundice.

A simpler method of bilirubin monitoring, requiring no blood-letting or other invasive procedures, would save time and money, spare infants the trauma of the "heel stick," and thus make practical the testing of all infants—not merely those already showing visible signs of jaundice—for elevated bilirubin. By eliminating the need for judgment calls by health professionals with varying levels of expertise, the method would permit more consistent measurements across time and would likely provide earlier detection of elevated bilirubin in some cases. Conceivably, by removing a major source of stress, such a method could also help save the lives of fragile premature infants.

SUMMARY OF THE INVENTION

According to its major aspects and broadly set forth, the present invention is a device for detecting bilirubin content of skin without invading the skin. The device comprises a light source that produces a light having a spectrum including a first portion or group of wavelengths that are absorbable by bilirubin and a second portion containing wavelengths not absorbable by bilirubin, means for transmitting light from this light source and directing it onto the skin of the infant and for receiving the reflected light, means for reducing the amount of the light absorbed by blood in the skin, and means for determining the amounts of light from each portion of the spectrum that have been absorbed by the skin. The two amounts are compared to ascertain the amount of bilirubin in the skin by how much light of one portion is absorbed compared to the other portion.

Preferably, to reduce the amount of light absorbed by hemoglobin in the skin's blood, a measurement is made on the skin of the kneecap and then on the skin of the forehead by pressing with sufficient force to drive out a substantial amount of the blood in the skin in the area being measured. To facilitate the careful application of force, the device has a handle assembly with a plunger and a spring, and a button in the housing having a set of embossed points which can be perceived with the fingers or hand of the user when sufficient force has been applied.

A fiber optic bundle connects the housing to the light source. The bundle has two ends, one end that has three separated bundles, one going to the light source and two going to circuitry for separately evaluating the amounts of light absorbed in each portion of the spectrum, and a second end where the three bundles of the first end are mixed or combined. The second end enters the housing, permitting light to be directed onto the skin and back into the bundle via a prism.

The amounts of light absorbed by each portion of the spectrum is determined by using two filters, and then directing the light passed by each onto a photocell that produces a signal proportional to the amount of incident, filtered light.

This device makes an accurate color comparison of two otherwise equivalent skin areas, one on the upper body and one on the lower. This comparison gives a reasonably good estimate of bilirubin deposition in the skin. While the resulting figures might not correlate closely with the blood levels now used as diagnostic criteria, this is probably not a serious drawback, since skin deposition is one step further along in the chain of pathology. Because of differences in liver maturity or other factors, different infants with equally high blood levels may not show the same degree of skin or brain deposition.

A feature of the present invention is a skin contact with provisions for application of sufficient pressure to force a substantial amount of blood from the skin in the area of the absorption measurement. As stated above, hemoglobin absorbs light and thus interferes to some extent with detection of bilirubin. Furthermore, blood distribution in the skin is uneven. These problems, however, may be alleviated by choosing skin sites where smooth bone lies near the surface—one site on the face or upper body and one on the lower—and applying enough pressure to squeeze out blood from the skin before comparison takes place. For simplicity, the chosen sites should be of roughly equal skin thickness so that the applied pressure may be the same for both. The forehead and the kneecap are two such sites. This method assures that the hemoglobin at each reading site will have been squeezed out of the skin uniformly, thus eliminating the hemoglobin interference.

Yet another feature of the present invention is a preferable, second light-sensing circuit included with a different wavelength of sensitivity, not absorbable by bilirubin, so that measurements may be corrected for the effects of the light source and light absorbing features of the skin. This feature is advantageous because it provides more reliable detection of bilirubin.

Yet another feature of an alternative embodiment of the present invention is the utilization of two light-emitting diodes (LED's), one of which emits blue light. Using LED light sources rather than an incandescent bulb increases reliability of the present invention because LED's do not normally burn out and their response changes less with age than that of incandescent sources. The narrow-band emission of LED's makes filters unnecessary. The fast response of LED's makes it possible to drive blue and yellow sources alternately, using a single photodiode to detect both beams and multiplexers or other techniques, rather than an integrated-circuit math block, to compare their intensities. Because filters, photodiodes, and a math block are more expensive components than a pair of LED'S, using LED's reduces the overall cost of the present embodiment considerably while increasing the reliability.

Other features and advantages of the present invention will be apparent to those skilled in the art from a careful reading of the Detailed Description of a Preferred Embodiment presented below and accompanied by the drawings.

DETAILED DESCRIPTION OF PREFERRED EMBODIMENTS

Figure 1:
FIG. 1 is a perspective of the preferred embodiment of the present invention, an optical transcutaneous bilirubin detector.
Figure 2:
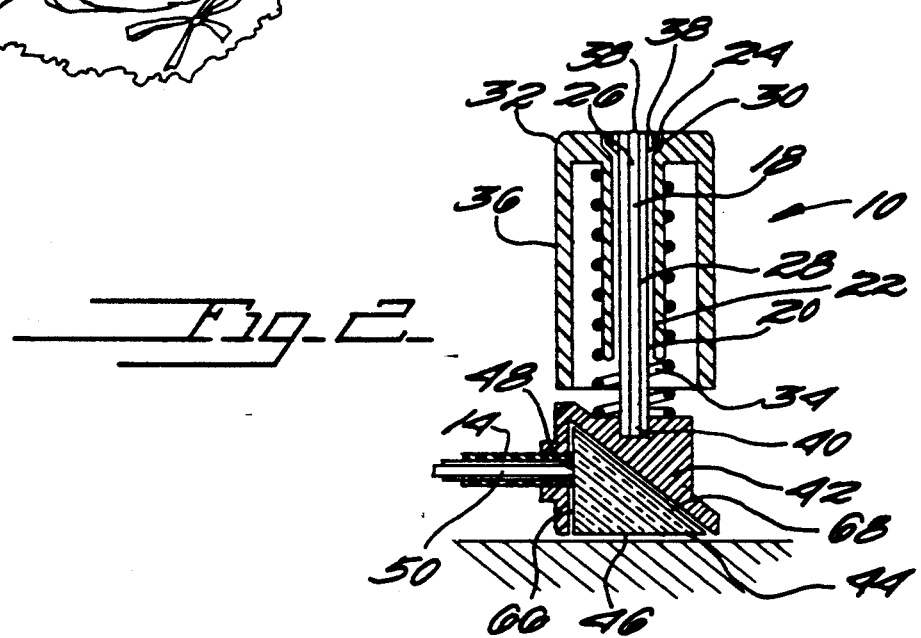
FIG. 2 is a cross-sectional view of the handle assembly of the present invention.
Figure 3:
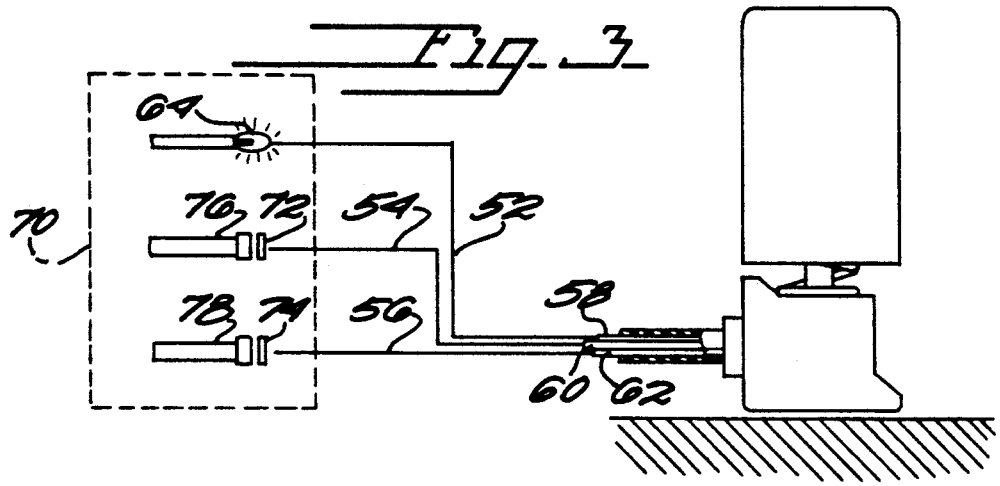
FIG. 3 is a schematic cross-sectional view of a first embodiment showing three optic fibers and filters.

Referring now to FIGS. 1, 2, and 3, a first embodiment of an optoelectronic device for measuring the level of bilirubin in the skin of infants (infantile jaundice) without requiring invasive medical procedures is shown generally by the reference character 10. Device 10 comprises handle assembly 12 and a fiber optic bundle 14 connecting handle assembly 12 to a light measuring circuitry 16. Handle assembly 12 contains a plunger 18 slidably received in a central opening 20 in the central tube 22 of handle assembly 12. Plunger 18 has an enlarged button 24 at one end 26 of its elongate member 28 designed to fit within a recess 30 in the top 32 of handle assembly 12. A spring 34 coiled about the central tube 22 holds button 24 within recess 30. Handle assembly 12 also contains an outer tube 36 which protects spring 34 and acts as a gripper for the user of device 10. Upon application of sufficient force to outer tube 36 of handle assembly 12, the force of spring 34 is overcome and handle assembly 12 moves downward so that button 24 protrudes beyond the top 32 of handle assembly 12. Button 24 is brightly colored and embossed with blunt points 38, while outer tube 36 is smooth and contrastingly colored, so that the rise of button 24 is easily perceptible to the hand or eye. The proper amount of force is signaled when the points 38 of button 24 just begin to protrude beyond the top 32 of handle assembly 12 and are perceived by the user: this is enough to force blood from the surface vessels, eliminating hemoglobin interference, without causing discomfort or bruising of the infant's fragile skin. At opposite end 40 of elongate member 28 is an opaque assembly 42 attached to a prism 44. Prism 44 is surrounded and protected by opaque assembly 42, leaving one face 46 of prism 44 exposed. Exposed face 46 is made to contact the skin of the infant. Opaque assembly 46 has an entry port 48 which receives a first end 50 of fiber optic bundle 14. Fiber optic bundle 14 consists of three groups of fibers 52, 54, 56 separated and enclosed by separate, opaque, flexible sheaths 58, 60, 62, respectively for most of their length, but united and randomly mixed at first end 50. A light source 64 is connected to fiber group 52 in such a way that its light is conducted down the bundle 14 to first end 50. Light source 64 is of a type which emits both blue and yellow light at roughly equal, substantially constant intensities and at an intensity ratio which is not strongly affected by operating conditions or lamp aging. A small incandescent lamp, either of the quartz-halogen type or with the filament surrounded by krypton gas, is suitable for this application.

At first end 50 where fiber groups 52, 54, 56 join, the individual fibers form a common end surface which is ground flat, polished, and cemented to prism face 66. The dimensions of prism 44 are only slightly larger than the diameter of first end 50. Light passing from light source 64 down group 52 of fiber optic bundle 14 enters prism 44 through face 66, is bent ninety degrees by reflection from face 68, and exits through face 46 to the infant's skin. Passing through the superficial layers, it is scattered back upward, passes again through face 46 and is reflected at face 68, and re-enters fiber optic bundle 14. A portion of this light passes up fiber group 54, and a corresponding portion up fiber group 56. Each of these groups enters a housing 70, which is preferably the same one which holds light source 64. Fiber group 54 ends against a filter 72 which selects a portion of the visible spectrum and reflects or, preferably, absorbs the remainder. Fiber group 56 ends against a filter 74 which selects a different portion of the visible spectrum and likewise reflects or, preferably, absorbs the remainder. Filter 72, attached to fiber group 54, passes only blue-violet light in the neighborhood of 453 nanometers, near the absorption peak of bilirubin; filter 74, attached to fiber group 56, passes yellow light in the neighborhood of 590 nanometers, which bilirubin absorbs only very weakly. Photocells 76 and 78 respectively monitor the intensity of the light passing through these filters and detected over a period of time. Filter 72 and photocell 76, and filter 74 and photocell 78, may, if desired, be combined into two units each consisting of a photocell and integral filter.

Figure 4:
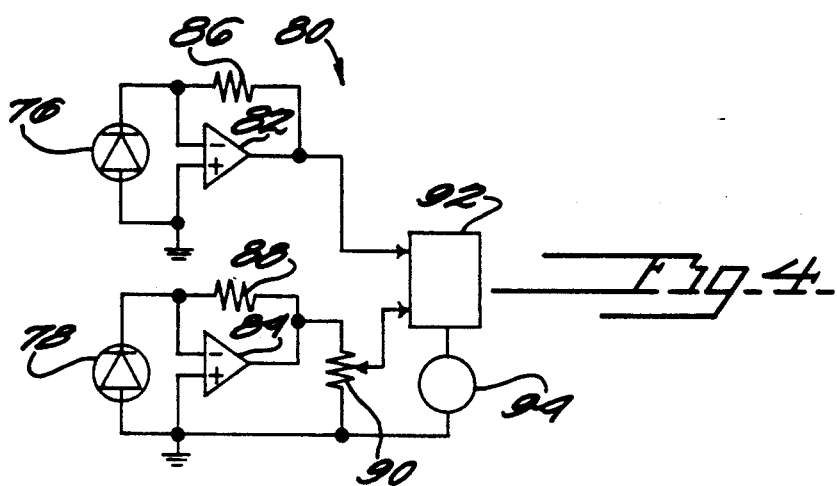
FIG. 4 is a circuit diagram of the embodiment of FIG. 3.

In FIG. 4, the light-measuring circuitry is referenced generally by the character 80. Circuitry 80 consists of photocells 76 and 78, the operational amplifiers 82 and 84, the fixed resistors 86 and 88, a continuously variable potentiometer 90, an analog math block 92 and a voltmeter 94. All components are powered by a pair of nine-volt radio batteries or by a small bipolar D.C. power supply, not shown. The current output from each photocell at zero voltage, which is proportional to light intensity, is converted to a voltage by the associated amplifier and fixed resistor. A portion of the voltage output from amplifier 84 (which will normally be higher than that from amplifier 82) is selected through potentiometer 90. Math block 92, which is preferably an LH0094 integrated circuit, takes the ratio of the voltages from amplifier 82 and potentiometer 90, expressing it as a voltage. This voltage is read by meter 94 which may be either analog or digital and is graduated from 0 to 100%.

In use, prism face 46 is pressed against the infant's kneecap until button 24 just protrudes from the top of the handle assembly, and potentiometer 90 is adjusted until meter 94 reads 100%. Device 10 is then removed from the kneecap and pressed against the infant's forehead. The new reading of meter 94 is recorded and compared with a chart, preferably located on device 10, which correlates the reading with approximate blood bilirubin levels. Only if a high level (low "%" reading) is indicated, or if for some reason it is not possible to set meter 94 at 100%, will a confirming "heel stick" and blood analysis be necessary.

Figure 5:
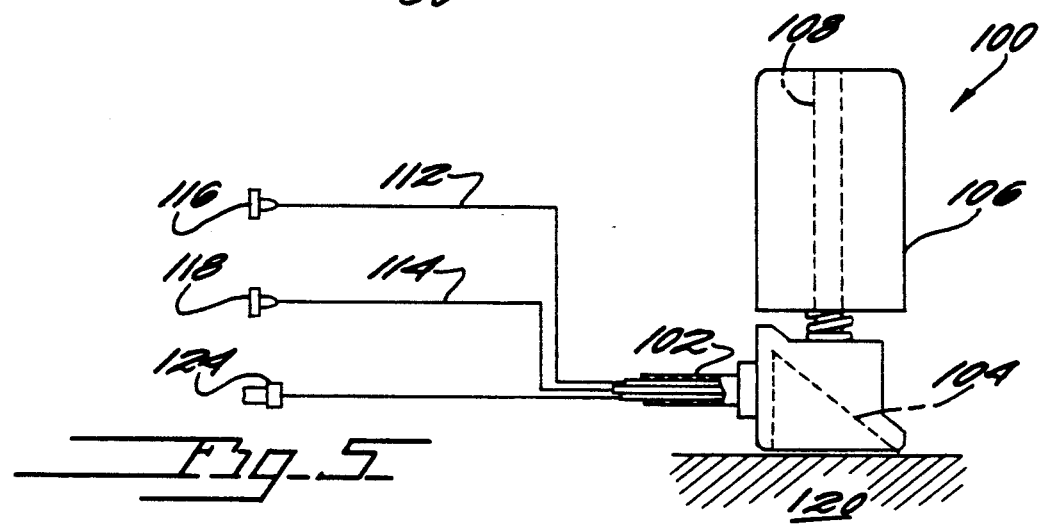
FIG. 5 is a second embodiment of the present invention showing three optic fibers and diodes capable of emitting yellow or amber and blue light.
Figure 6:
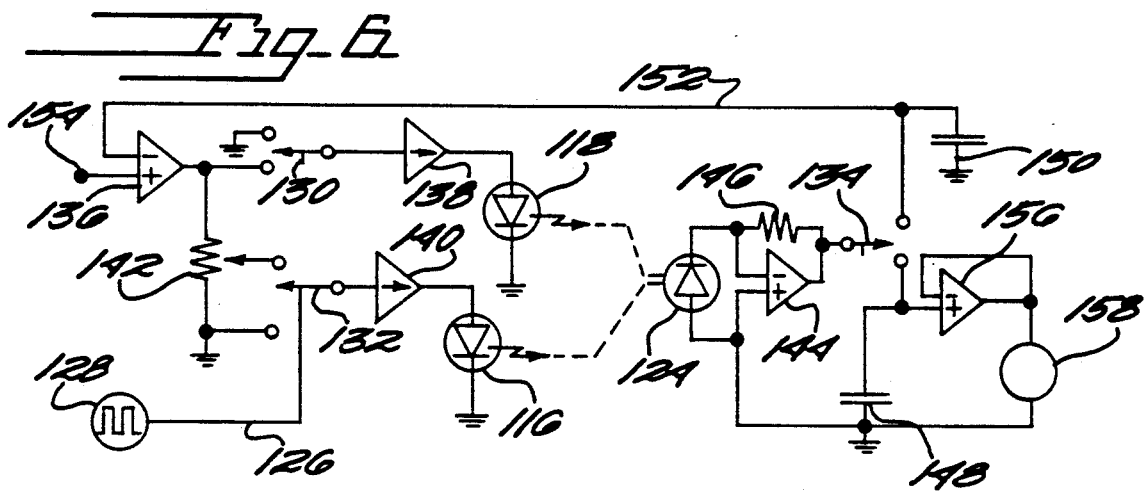
FIG. 6 is a circuit diagram of the embodiment of FIG. 5.

Referring to FIG. 5, a second embodiment of the present invention is illustrated by reference numeral 100. Device 100 uses an identical fiber optic bundle 102, prism 104, and handle assembly 106 containing a spring-loaded plunger 108, as were described in the first embodiment with reference to FIGS. 1, 2, and 3. The present embodiment of device 100 differs in the following ways.

To branches 112 and 114 of fiber optic bundle 102 are attached light-emitting diodes (LED's) 116 and 118. Of these, LED 116 is an ordinary, yellow or amber LED having peak emission around 585 nanometers, while LED 118 is a blue LED with peak emission around 470 nanometers. Light from both of these LED's is conducted through fiber optic bundle 102 to prism 104, reflected from the infant's skin 120, and returned through branch 122 of bundle 102 to a single, unfiltered photodiode 124 capable of detecting both blue and yellow light. A square-wave signal 126, produced by circuit 128 embodying any one of the many well-known square-wave generation means, controls relays, or preferably, solid-state analog switches 130, 132, and 134. These switches may be, for example, the three sections of an MC14053 CMOS analog multiplexer chip. The output voltage of an operational amplifier 136 is fed to two voltage-controlled current sources 138 and 140; to source 138 directly, and to source 140 through a voltage divider 142. Sources 138 and 140 may, for example, be Howland-type current sources each yielding five milliamperes per volt. Sources 138 and 140 drive LED's 116 and 118, respectively, so that when one is on, the other is off. As a result, LED's 116 and 118 are alternately driven, producing a sequence of alternating blue and yellow light flashes at prism 104.

Light reflected from the infant's skin is detected by photodiode 124 which, in combination with an amplifier 144 and a fixed resistor 146, produces a train of alternating analog voltage levels which correspond to the intensities of the blue and yellow reflected light pulses. Switch 134, operating synchronously with switches 130 and 132 which produce the flashes, separates and directs these voltages to two low-leakage storage capacitors 148 and 150, which hold the "blue" and "yellow" voltages respectively. The "yellow" voltage travels back by a feedback path 152 to operational amplifier 136, where it is compared with a reference voltage 154; amplifier 144's output changes in such a way as to keep the sensed "yellow" output signal constant. The "blue" voltage is buffered by an amplifier 156 and read by a meter 158, which is graduated in "percent."

All components of the invention are supplied by a low-voltage D.C. power supply or by batteries, not shown.

When placed against the infant's kneecap, voltage divider 142 is adjusted so that meter 158 reads "100%", indicating that the ratio of LED output intensities is such that equal voltages appear on capacitors 148 and 150. It is assumed in the circuit design that, because of lower skin reflectivity in the blue part of the spectrum and probably lower quantum efficiency in the blue LED, the drive current for LED 118, and thus the control voltage for current source 140, will have to be higher than their "yellow" counterparts. When "100%" is read, the invention is removed from the infant's kneecap and placed on the forehead. Amplifier 136 automatically adjusts the yellow LED intensity so that the same intensity of reflected yellow light is read. This compensates for any changes in light coupling which might result from differences in skin texture, moisture, or the like. Since the blue LED current maintains a constant ratio with the yellow, any change in the detected level of blue light, and hence in the meter reading, signals a difference in the blue-yellow reflectivity ratio and hence the probable presence of bilirubin in the skin.

It will be apparent to those skilled in the art that many changes and substitutions can be made to the preferred embodiment herein described without departing from the spirit and scope of the present invention which is defined by the appended claims.

What is claimed is:

1. A device for measuring bilirubin content of skin, said device comprising:
    a handle assembly;
    a source of light having a first portion containing light of wavelengths absorbed by bilirubin and a second portion containing light of wavelengths not absorbable by bilirubin;
    means carried by said handle assembly and in optical communication with said source of light for directing said light onto said skin when pressed against said skin, said directing means receiving light reflected by said skin;
    means in optical communication with said directing means for receiving said reflected light for determining said amount of bilirubin in said skin by comparing a measured amount of said first portion of said reflected light to a measured amount of said second portion of said reflected light;
    a button slidably carried within said handle assembly, said button having a recessed position and a protruding position; and
    means for biasing said button in said recessed position,
    said button moving to said protruding position from said recessed position as said device is pressed against said skin, said button reaching said protruding position when sufficient pressure has been applied to said skin with said device.

2. The device as recited in claim 1, wherein said determining means further comprises:
    a blue filter;
    a yellow filter;
    first means in spaced relation to said blue filter for measuring a first amount of light passing through said blue filter;
    second means in spaced relation to said yellow filter for measuring a second amount of light passing through said yellow filter; and
    means in electrical communication with said first and second measuring means for comparing said first amount to said second amount of light.

3. A device for measuring bilirubin content of skin, said device comprising:
    a handle assembly;
    a source of light having a first portion containing light of wavelengths absorbed by bilirubin and a second portion containing light of wavelengths not absorbable by bilirubin, said light having a substantially constant intensity;
    means carried by said handle assembly and in optical communication with said source of light for directing said light onto said skin, said directing means receiving light reflected by said skin;
    means in optical communication with said directing means for receiving said reflected light for determining said amount of bilirubin in said skin by comparing a measured amount of said first portion of said reflected light to a measured amount of said second portion of said reflected light;
    a button slidably carried within said handle assembly, said button having a recessed position and a protruding position; and
    means for biasing said button in said recessed position,
    said button moving to said protruding position from said recessed position as said device is pressed against said skin, said button reaching said protruding position when sufficient pressure has been applied to said skin with said device.

4. The device as recited in claim 3, wherein said determining means further comprises:
    a blue filter;
    a yellow filter;
    first means in spaced relation to said blue filter for measuring a first amount of light passing through said blue filter;
    second means in spaced relation to said yellow filter for measuring a second amount of light passing through said yellow filter; and
    means in electrical communication with said first and second measuring means for comparing said first amount to said second amount of light, said first and said second amounts of light measured over a period of time.

* * * * *